United States Patent
Herskowitz

(10) Patent No.: US 7,351,226 B1
(45) Date of Patent: Apr. 1, 2008

(54) MEDICAL INFUSION PUMP

(76) Inventor: Glenn Herskowitz, P.O. Box 5155, Larkspur, CA (US) 94977

( * ) Notice: Subject to any disclaimer, the term of this patent is extended or adjusted under 35 U.S.C. 154(b) by 0 days.

(21) Appl. No.: 11/007,148

(22) Filed: Dec. 7, 2004

(51) Int. Cl.
*A61M 37/00* (2006.01)

(52) U.S. Cl. .................................... 604/141

(58) Field of Classification Search ........ 604/140–143, 604/131, 134, 153, 146, 151, 147
See application file for complete search history.

(56) References Cited

U.S. PATENT DOCUMENTS

| | | | | |
|---|---|---|---|---|
| 2,631,088 | A | * | 3/1953 | Guild ........................... 422/88 |
| 4,684,367 | A | * | 8/1987 | Schaffer et al. .............. 604/140 |
| 4,741,736 | A | | 5/1988 | Brown |
| 5,106,374 | A | | 4/1992 | Apperson et al. |
| 5,330,431 | A | * | 7/1994 | Herskowitz .................. 604/153 |
| 5,348,539 | A | * | 9/1994 | Herskowitz .................. 604/141 |
| 5,520,639 | A | * | 5/1996 | Peterson et al. ............... 604/68 |
| 5,549,672 | A | * | 8/1996 | Maddock et al. ............... 623/8 |
| 5,554,123 | A | * | 9/1996 | Herskowitz .................. 604/141 |
| 5,681,284 | A | * | 10/1997 | Herskowitz .................. 604/141 |
| 5,954,696 | A | * | 9/1999 | Ryan ........................... 604/141 |
| 6,641,562 | B1 | * | 11/2003 | Peterson ....................... 604/141 |
| 2004/0064097 | A1 | * | 4/2004 | Peterson ....................... 604/132 |

* cited by examiner

*Primary Examiner*—Kevin C. Sirmons
*Assistant Examiner*—Catherine N. Witczak
(74) *Attorney, Agent, or Firm*—Thomas M. Freiburger

(57) ABSTRACT

An infusion pump for infusing solutions from IV bags, particularly large one liter bags, through tubing to patients includes housing that has a compartment to receive an IV bag in a solution-dispensing position. The bag rests over a bladder within the compartment, and the bladder is expanded by a pressurized fluid to apply a pushing force against the bag to force solution through the tubing at a prescribed pressure. The fluid for the bladder is pressurized by a pump controlled by a control circuit that includes a pressure sensor sensing pressure of the fluid in the bladder. A preferred form of the infusion pump includes a high-pressure gas cartridge in a parallel and redundant system for applying pressure in the bladder. The fluid pump for the bladder preferably is powered by batteries, and in the event battery power is lacking, the gas cartridge (which may be $CO_2$), which is regulated down in pressure, can be used to supply the needed pressure (if a small auxiliary battery is included to operate valves and circuitry). Another feature is a universal solution bag spike/port adapter, with a "bag/spike present" switch that is operable when a bag with a port in any of a plurality of different positions is placed in the compartment, accommodating the bags of nearly all manufacturers. When a new solution bag is to be placed in the housing's compartment, an external vent port may be opened manually for quick venting of the bladder. In addition, the unit preferably includes an exterior indicator of pressure level in the gas cartridge, for easy reference as to whether this redundant system is operable.

20 Claims, 9 Drawing Sheets

MEDICAL INFUSION PUMP

BACKGROUND OF THE INVENTION

This invention concerns delivery of intravenous (IV) solutions to a patient, and is particularly concerned with an infusion pump which applies pressure to a solution bag, which may be a large solution bag, for delivering solution under pressure through tubing to a patient. A portable such infusion pump is a preferred embodiment of the invention.

The subject matter of this invention is related to U.S. Pat. No. 5,681,284, commonly owned with this invention, as well as U.S. Pat. Nos. 4,741,736, 5,330,431 and 5,348,539. As discussed in that patent, infusion pumps are used to deliver various types of solutions intravenously to patients. A variety of drugs are commonly administered to patients by means of intravenous solutions. Among the types of therapies requiring this kind of administration are chemotherapy, antibiotic therapy and antiviral therapy. In many cases, patients receive multiple daily therapies. Certain medical conditions require infusion of drugs in solution over relatively short periods of time, such as from 30 minutes to 2 hours. Infusion pumps have been developed in the prior art in an effort to meet these needs. There has been a requirement of providing portable infusion pumps for use in ambulances and other emergency situations, and by ambulatory patients.

Different types of infusion pumps in the prior art include elastomeric pumps which squeeze the solution from flexible containers, such as bags or balloons, into IV tubing for delivery to the patient. Spring-loaded pumps have also been provided to pressurize the solution containers or reservoirs. In certain infusion pump designs, cartridges containing flexible compound compartments that are squeezed by pressure rollers for discharging the solutions are provided, such as in U.S. Pat. No. 4,741,736. U.S. Pat. No. 5,330,431, issued to the inventor of the present invention, shows an infusion pump in which standard prefilled single dosage IV bags are squeezed by the use of a roller. U.S. Pat. No. 5,348,539, also issued to the inventor of the present invention, shows an infusion pump in which prepackaged IV bags are squeezed by a bladder which is actuated by a fluid pump from a reservoir.

Dispensing spikes have been provided for interconnecting IV tubing with the IV bags. The spikes penetrate through dispensing ports in the bags to permit the fluid to infuse through the tubing to the patient. U.S. Pat. No. 5,106,374 to Apperson discloses a spike having a locating flange which assists in locating the spike within the housing of an ambulatory infusion device.

The prior art infusion devices include arrangements for sensing the pressure of the IV bags to control the infusion procedure, such as for shutting off the infusion flow.

A portable infusion pump of the '284 patent controls the infusion process by indirectly sensing IV solution pressure without intrusion into the bag itself. Also that infusion pump provides a safe and reliable arrangement for sensing when the IV bag is in its proper solution-dispensing position within the compartment of the pump housing and ensures that the dispensing spike cannot be accidentally withdrawn from the bag's dispensing port when the infusion is in progress.

There is a need for an IV infusion pump, particularly a portable infusion pump, which can dispense solution from larger one liter solution bags particularly for emergency situations, and which has versatility and redundancy in operation so as to have alternative pressure sources for situations when needed. In addition, a universal such implement is needed, to receive IV, solution bags from different manufacturers, having two or three different port positions. Further, there is often a need for quick venting of the infusion pump's bladder that puts pressure on the IV bag, so that a new IV bag can be quickly installed.

SUMMARY OF THE INVENTION

In accordance with this invention, an infusion pump for infusing solutions from IV bags, particularly large one liter bags, through tubing to patients includes a housing that has a compartment to receive an IV bag in a solution-dispensing position. The bag rests over (or under) a bladder within the compartment, and the bladder is expanded by a pressurized fluid to apply a pushing force against the bag to force solution through the tubing at a prescribed pressure. The fluid for the bladder is pressurized in either or both of two ways: a pump controlled by a control circuit that includes a pressure sensor sensing pressure of the fluid in the bladder; and a high-pressure gas cartridge in a parallel and redundant system for applying pressure in the bladder, also controlled by the control circuit. The fluid pump for the bladder preferably is powered by batteries. In the event the electric pump becomes inoperative, the compressed gas cartridge (which may be air, $CO_2$, etc.), regulated down to a lower pressure, still supplies the needed pressure. Both pressure sources can be operable simultaneously and redundantly, or one of them can be a primary pressure source. If desired a back-up battery can be included to operate valves, sensors and indicator lights, in the event the pump-powering battery goes out and pressure is supplied solely by the gas cartridge.

Another feature is a universal solution bag/spike port adapter, with a "bag present" switch that is operable when a bag with a port in any of a plurality of different positions is placed in the compartment, accommodating the bags of nearly all manufacturers. When a new solution bag is to be placed in the housing's compartment, an external vent port may be opened manually for quick venting of the bladder. In addition, the unit preferably includes an exterior indicator of pressure level in the gas cartridge, for easy reference as to whether this redundant system is operable.

In one preferred embodiment an infusion pump for delivering intravenous solution from a solution bag through tubing to a patient comprises a housing with a compartment for removably receiving and supporting the intravenous solution bag in a solution-dispensing position, and an expandable bladder within the compartment, having a flexible wall which moves by expansion responsive to an increase in the pressure of a fluid within the bladder. The bladder is positioned in the housing so as to apply a pushing force against the flexible wall of a solution bag when present, to progressively collapse the solution bag responsive to expansion of the bladder wall to cause solution within the bag to be infused out through the dispensing port. A sensor determines pressure in a solution bag when present (indirectly, by sensing pressure in the bladder), and an electric pump is connected to pump fluid into the bladder to increase pressure in the bladder in response to a signal derived from the sensor and indicating the need for increased pressure. A gas cartridge containing high-pressure gas is preferably also connected to the housing, with a pressure regulator connected to the gas cartridge to produce gas at greatly reduced pressure, followed by a flow restrictor, the reduced-pressure gas being connected to the bladder in parallel with the electric pump. If one of the pressure sources is primary, then the other may be automatically activated when the primary cannot function. A control means is connected to the sensor and is effective to activate both the electric pump and a valve in the path of the reduced-pressure gas, if both act simultaneously in parallel, to send fluid to the bladder to increase pressure in the bladder when the sensor indicates pressure in the bladder is below a desired pressure preselected in the control means.

In a preferred embodiment the pressurized gas cartridge has a means for screwing onto the housing to receive the cartridge at the exterior of the housing, for easy replacement.

In a preferred embodiment the electric pump and the reduced pressure gas from the cartridge are both connected to deliver fluid (air or a gas) to the bladder, both working simultaneously whenever the control means send a signal to inflate the bladder. If either the pump fails or the gas cartridge loses pressure, the other pressure source serves a redundant function. As noted above a small back-up battery can be included to maintain power to control valves, indicator lights, etc.

As noted above the invention preferably includes a visual indicator of pressure remaining in the gas cartridge. This may be, for example, a needle whose position changes to reflect remaining pressure, or a protrusion that extends out of the housing to a different degree reflecting remaining gas pressure.

It is thus among the objects of the invention to provide an improved medical infusion pump for delivering intravenous solutions to a patient, particularly an efficient infusion pump that applies pressure to a solution bag, including one-liter bags, to deliver solution under pressure through tubing, and preferably with redundant systems for supplying that pressure, and with other features as described above. These and other objects, advantages, features and characteristics of the invention will be apparent from the following description of a preferred embodiment, considered along with the drawings.

DESCRIPTION OF PREFERRED EMBODIMENTS

Figure 1:
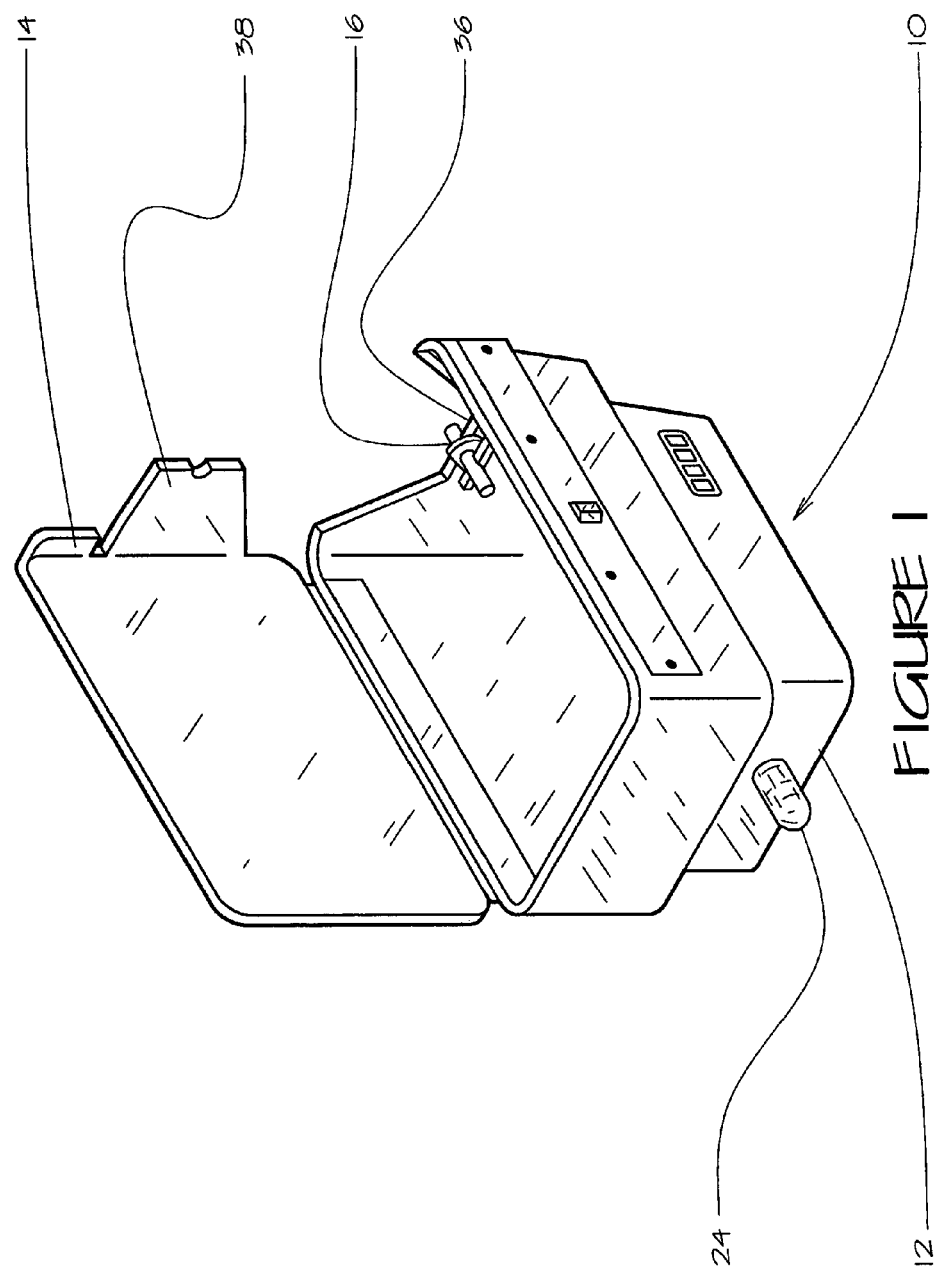
FIG. 1 is a perspective view showing a medical infusion pump according to the invention, with a cover of the housing in opened position.

FIG. 1 shows a medical infusion pump unit 10 according to a preferred embodiment of the invention, with a housing 12 and showing a hinged cover or lid 14 open to receive an intravenous solution bag. FIG. 1 shows a spike 16 which would be at the end of an IV tube (tube not shown), with the spike seated in a port adapter of the invention, to be described below.

Figure 2:
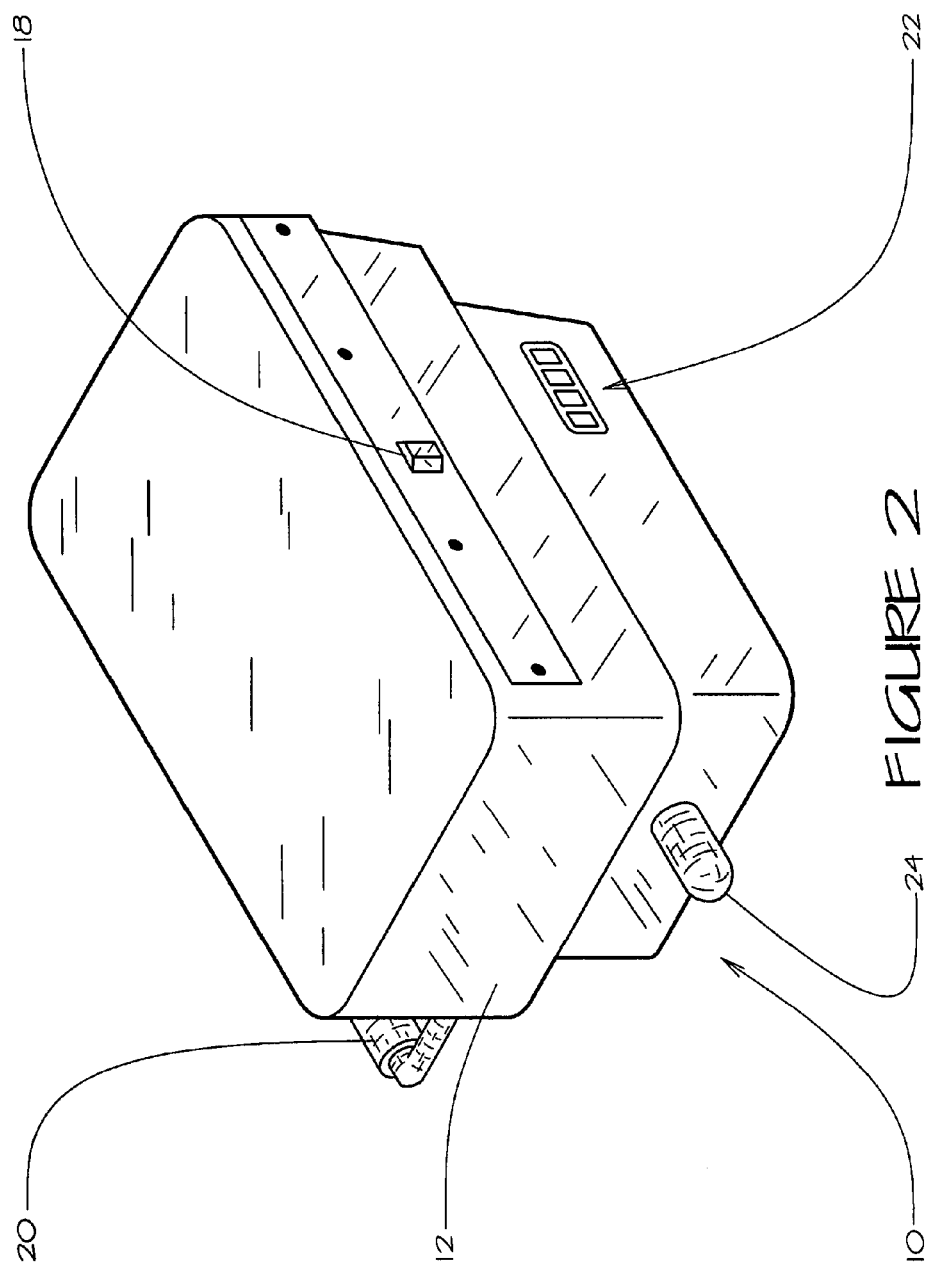
FIG. 2 is a perspective view showing the housing of the infusion pump.

In FIG. 2 the unit 10 is shown in a perspective view, with the cover held closed by a latch 18 on one side of the unit. A carrying handle 20 is shown on the opposite side of the portable infusion pump unit. Controls and status indicators are shown at 22, and a compressed gas cartridge 24 is seen at one side of the housing 12, screwed into the housing as a redundant pressurizing system for pressurizing IV solution bags to deliver IV liquid.

Most of the components and operation of the infusion pump unit 10 are the same as described in U.S. Pat. No. 5,681,284, which is incorporated herein.

Figure 3:
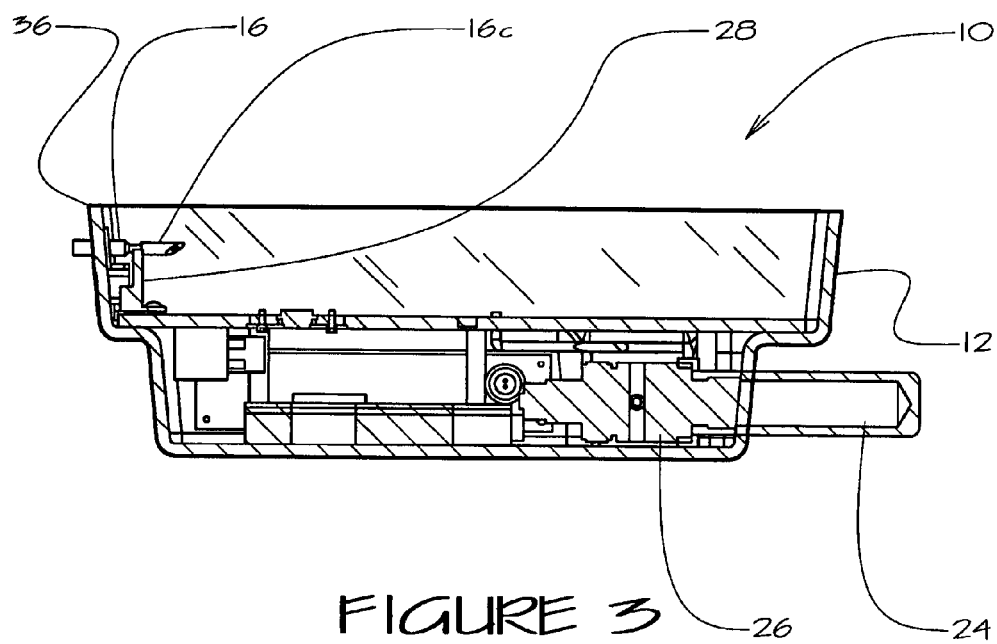
FIG. 3 is a side view of the infusion pump in longitudinal cross section.

FIG. 3 shows in cross section the unit housing 10, without the cover. The compressed gas cartridge (e.g. a $CO_2$ cartridge 24, or a canister/housing 24 which is threaded and designed to engage the gas cartridge against the housing into an operating mode), is shown secured to an internal component 26 which is a pressure regulator/reducer. Other internal components will be discussed below.

Figure 3A:
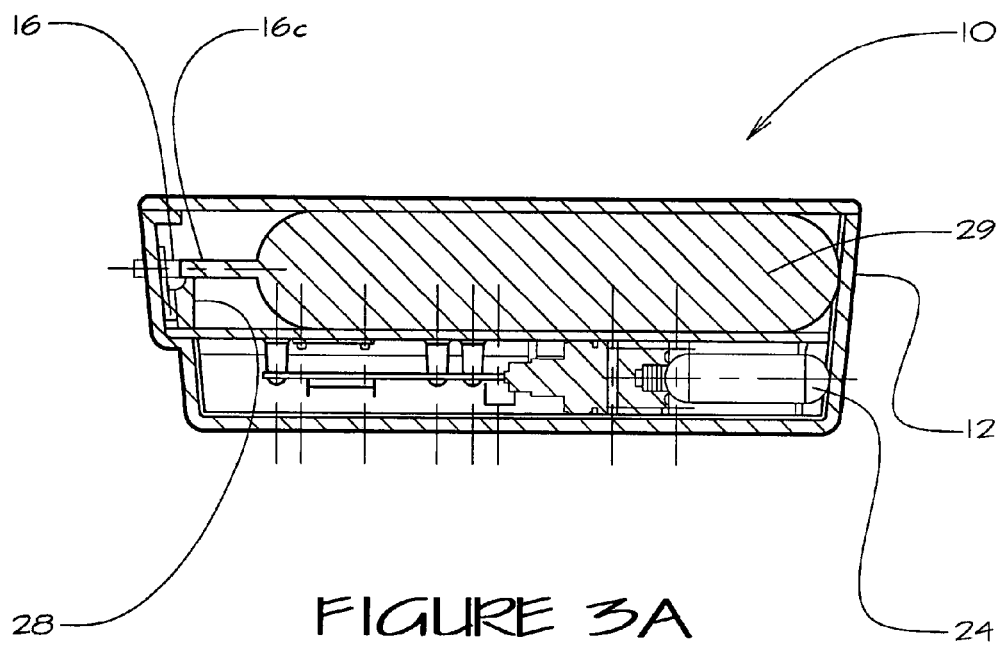
FIG. 3A is a view similar to FIG. 3 but showing a solution bag in the housing.

FIG. 3 illustrates in side view a dispensing spike 16 from an IV tube (not shown), as in FIG. 1, engaged in a dispensing port 16c of a bag, and showing the dispensing spike/port resting on an adapter 28 inside the housing. FIG. 3A shows a solution bag 29 in the housing.

Figure 4:
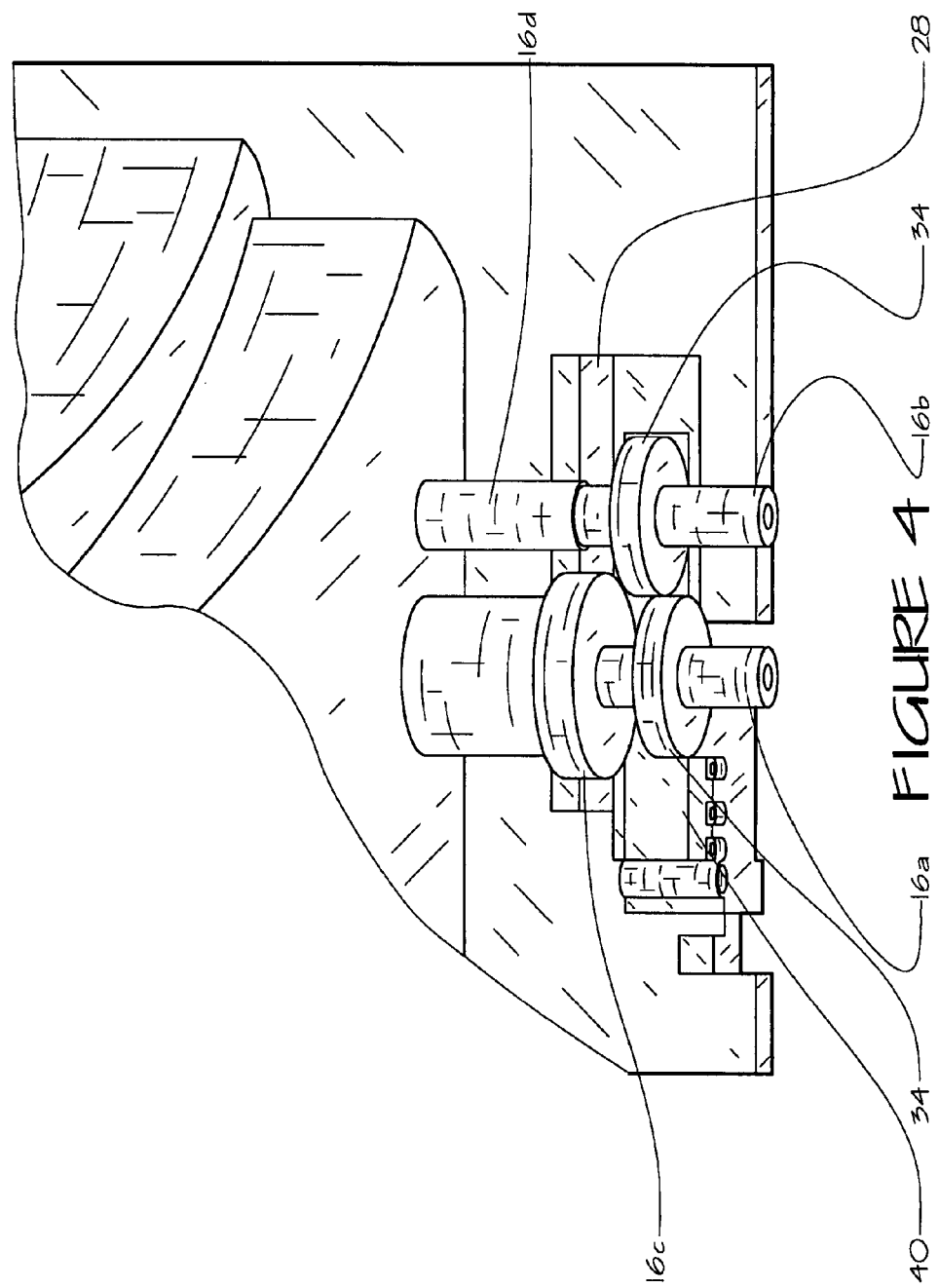
FIGS. 4 and 5 are perspective views showing a universal bag spike/port adapter of the infusion pump, accommodating several different configurations of bag spikes.
Figure 5:
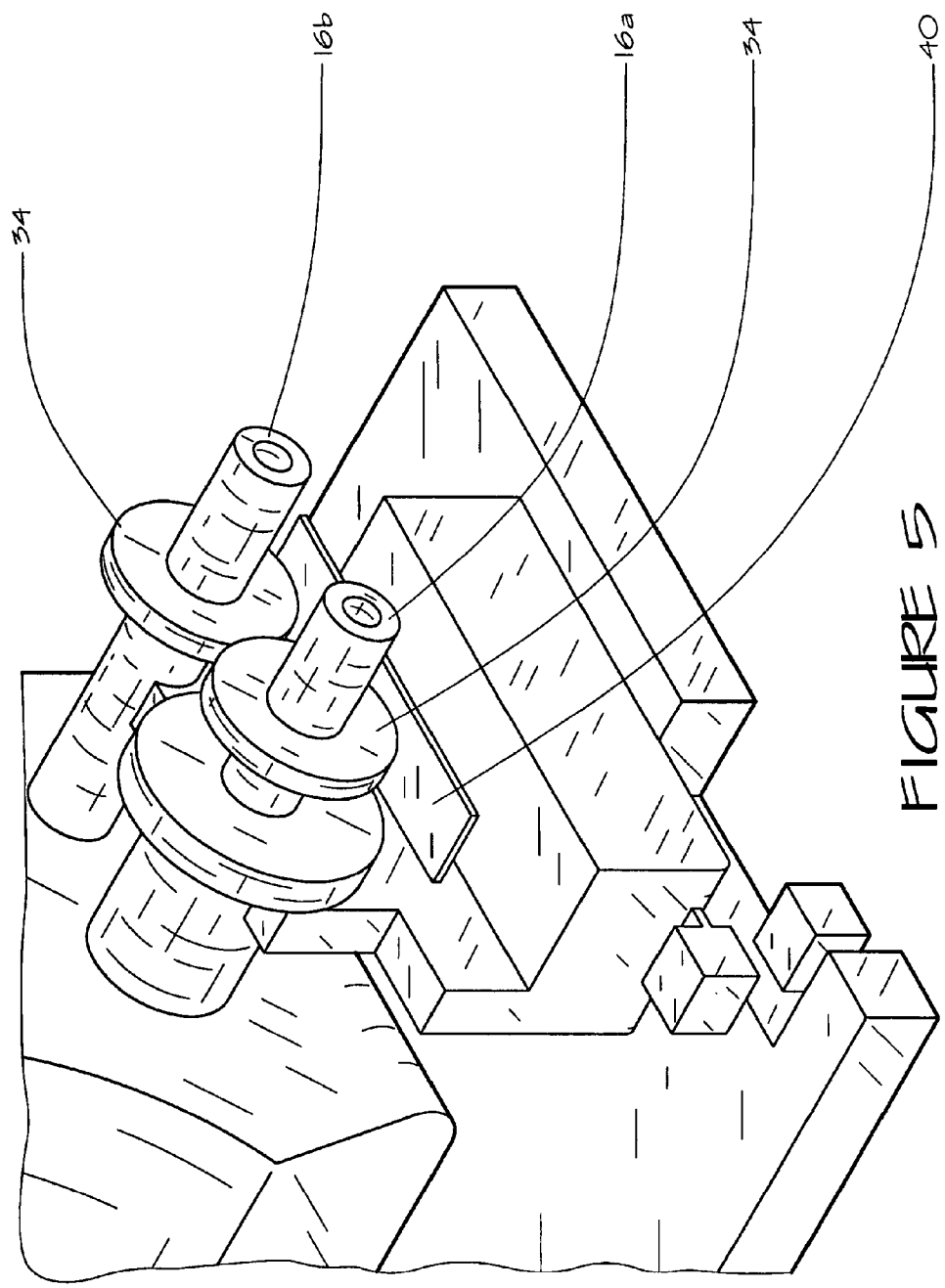
Figure 6:
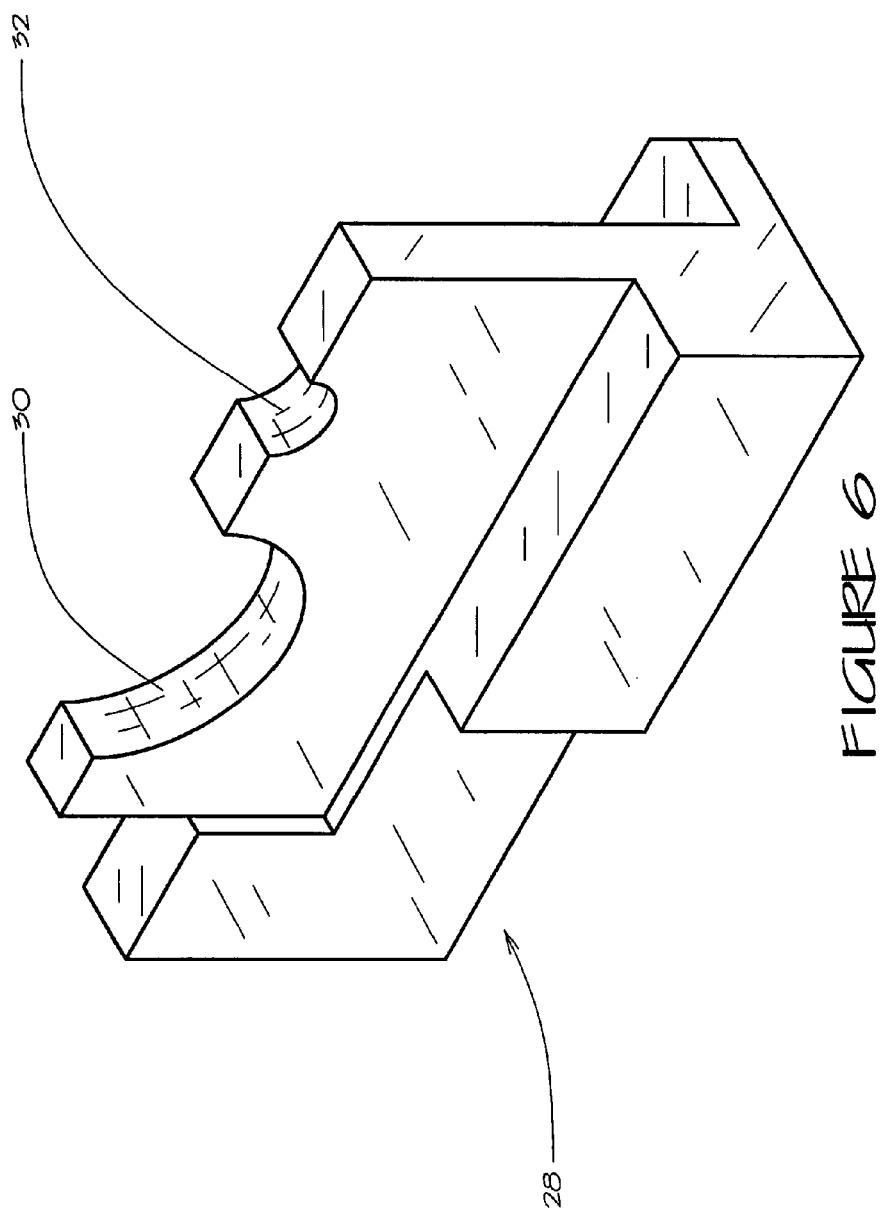
FIG. 6 is a perspective view showing a portion of the universal bag spike/port adapter.

FIGS. 4, 5 and 6 also show the adapter 28, in somewhat schematic views. In FIG. 4 dispensing spikes 16a and 16b are shown connected into bag ports 16c and 16d resting on the adapter 28, in respective notches 30 and 32 which are seen in FIG. 6. Only one such dispensing spike is present at any one time, since each IV solution bag has only one dispensing port which the spike penetrates. FIGS. 4 and 5 merely show that bags with different ports at different locations (and different outside diameters) can be accommodated. FIG. 5 shows the same arrangement as FIG. 4 from a different angle. In both cases the dispensing spike 16a or 16b from the IV tubing includes an enlarged annular collar 34 which helps enable the hand of the user to push the dispensing spike with sufficient force to engage it into the dispensing port associated with the IV solution bag, the port being shown at 16c or 16d in FIGS. 4 and 5. These enlarged collars 34, as in U.S. Pat. No. 5,681,284, also cooperate with an end wall 36 (FIGS. 1, 3) of the housing 12, and a wall 38 attached to the cover 14, to capture and hold the tubing and dispensing spike in place when the bag is in the proper solution-dispensing position.

As can be seen in FIGS. 4 and 5, the proper positioning of the bag, dispensing port and IV dispensing spike will engage a switch by the annular collar's (34) engaging against and pushing down a switch actuator 40, and the actuation of this switch enables the system to operate to dispense solution. This is also similar to the patent referenced above, except that the switch actuator 40 is longer in length and positioned and shaped to be engaged by dispensing spike collars 34 of any of a number of different solution bags that are available. Although not shown clearly in FIGS. 4 and 5, the switch actuator 40 is directly under the collar 34 (at one of the two positions shown) and may be shaped irregularly to engage properly with the collar diameter associated with a particular bag.

Figure 7:
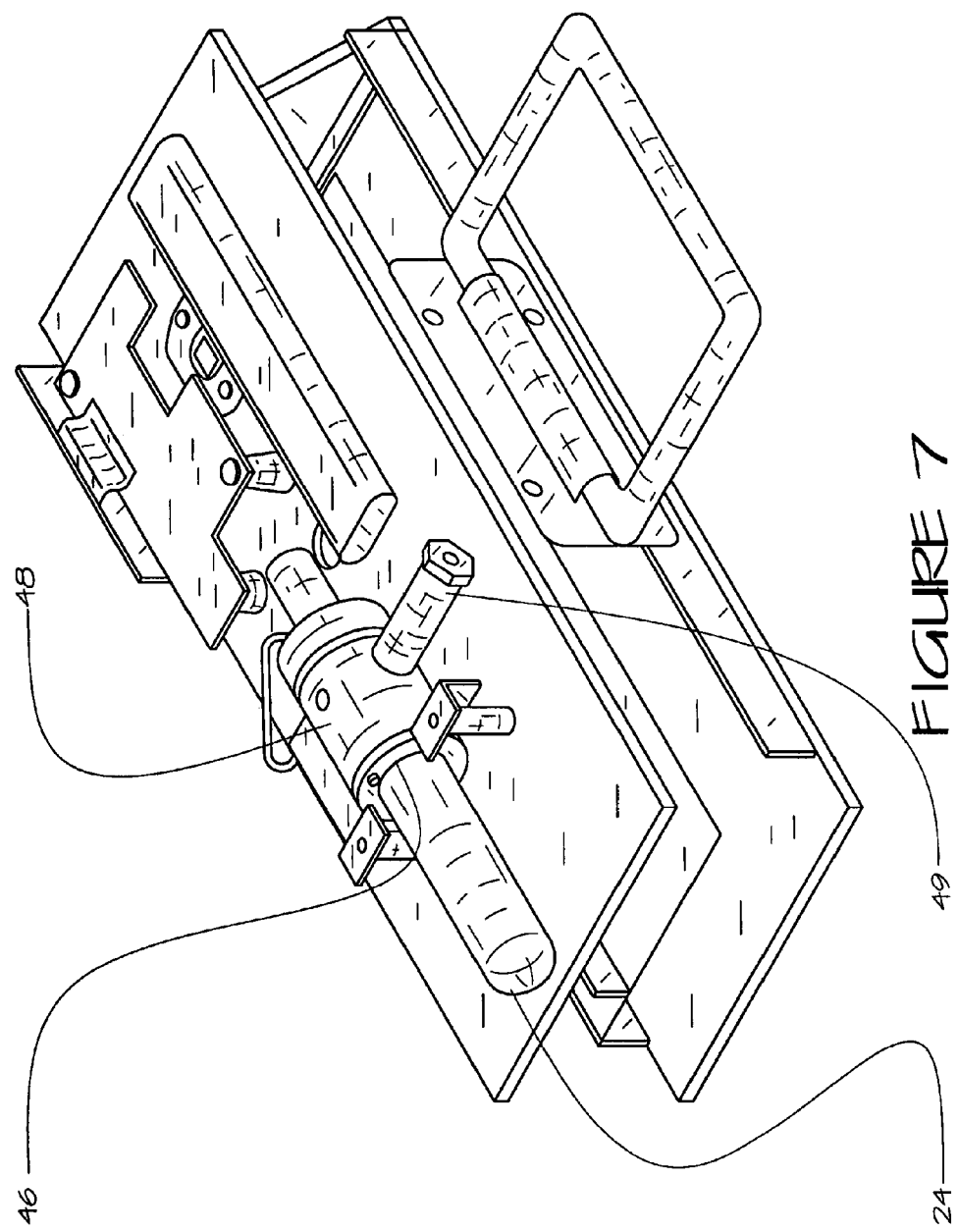
FIG. 7 is a perspective view showing some of the components of the invention, with most of the housing removed.
Figure 8:
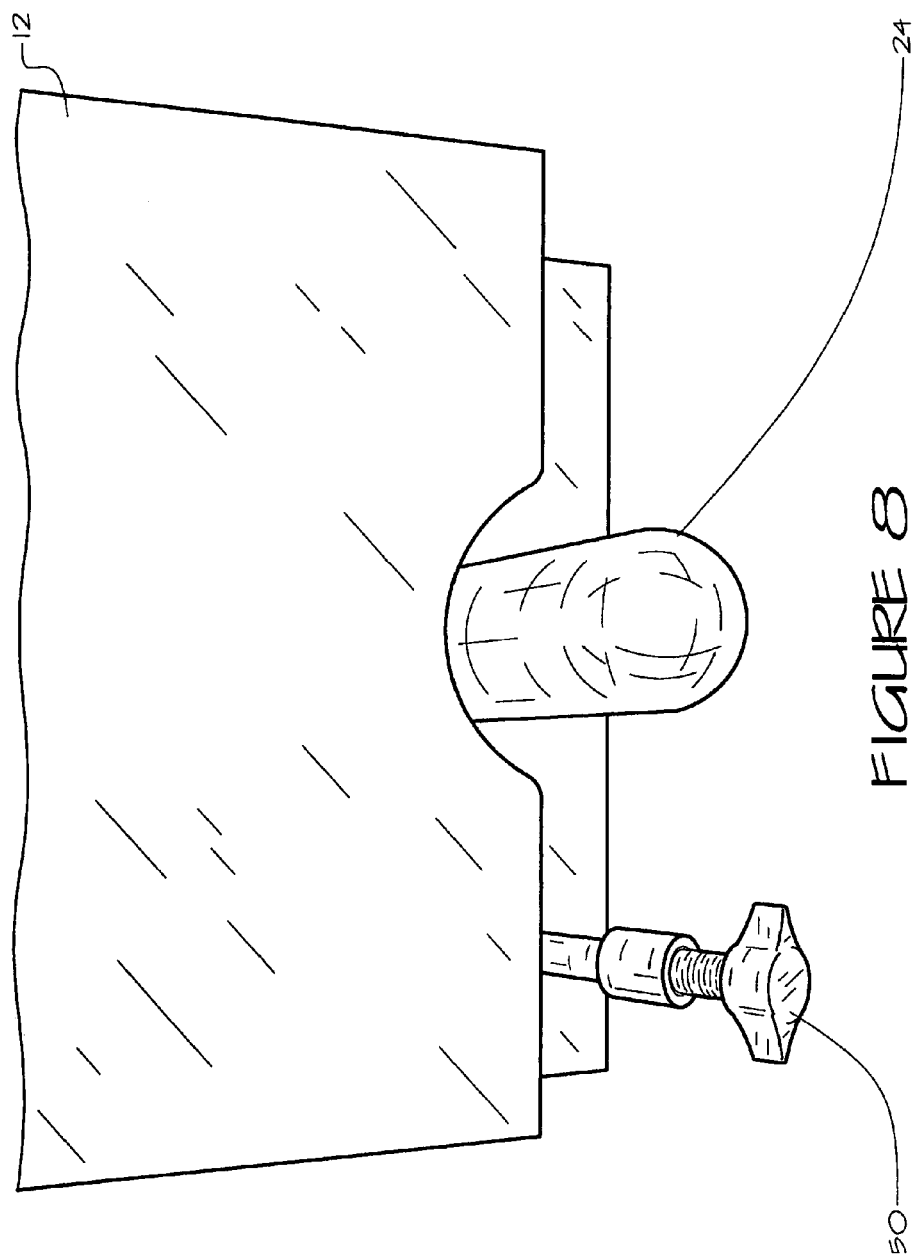
FIG. 8 is a perspective view from one end of the infusion pump, showing several features of the invention.

FIGS. 7 and 8 show other features of the invention, particularly in relation to a gas cartridge included in the infusion pump device of the invention as a redundant system. FIGS. 7 and 8 show the gas cartridge 24, or a housing which engages over the compressed gas cartridge, extending from an end of the housing 12 of the unit (housing not shown in FIG. 7). Either the cartridge itself (such as a $CO_2$ cartridge or other compressed gas) has threads and engages directly into a thread fitting 46 in the housing to break the seal of the cartridge, or a generally cylindrical cartridge-engaging housing or canister or capsule is threaded and connects into the threaded fitting 46 in the unit to force the cartridge into the gas-dispensing mode. In either event, the gas cartridge 24 preferably is accessible from the exterior of the unit, for convenience in changing the cartridge when needed. It engages into a pressure regulator 48 which greatly reduces pressure. This is also indicated in the control-flow diagram of FIG. 9.

When remaining pressurized gas in the cartridge 24 is low, the unit 10 preferably includes an indicator which readily reveals this to the operator. This can be in the form of a plunger device 49 (FIG. 7) that extends at the exterior of the unit, to a varying degree depending on the remaining pressure, connected to the high pressure side of the regulator 48 and urged in the opposite direction, against the cartridge pressure, by a spring or opposing gas pressure. It could otherwise be a simple needle gauge, with the position of the needle controlled by pressure against a spring, or any other suitable device. The indicator could be on either side, but it is more preferably located on the front side of the housing where the operator controls and indicators 22 are located (FIGS. 1 and 2).

FIG. 8 also shows a manually operated screw cap or manually operated valve 50, which acts as a manual external relief valve. This is shown schematically in FIG. 9, where the relief valve or cap 50 is shown connected by a gas line 52 into a bladder 54 which provides fluid pressure for pressurizing an IV solution bag 29 within the housing 12 of the unit. This bag pressuring arrangement is similar to what is disclosed in the above referenced '284 patent. The relief line and valve 52, 50 enable an operator quickly to vent the air or gas from the bladder 54 when a new, full IV bag is to be placed in the housing, rather than having to push the bladder down to remove its fluid contents through a line 56 and through a longer route to atmosphere. The IV solution bag can be more quickly replaced in this way.

Figure 9:
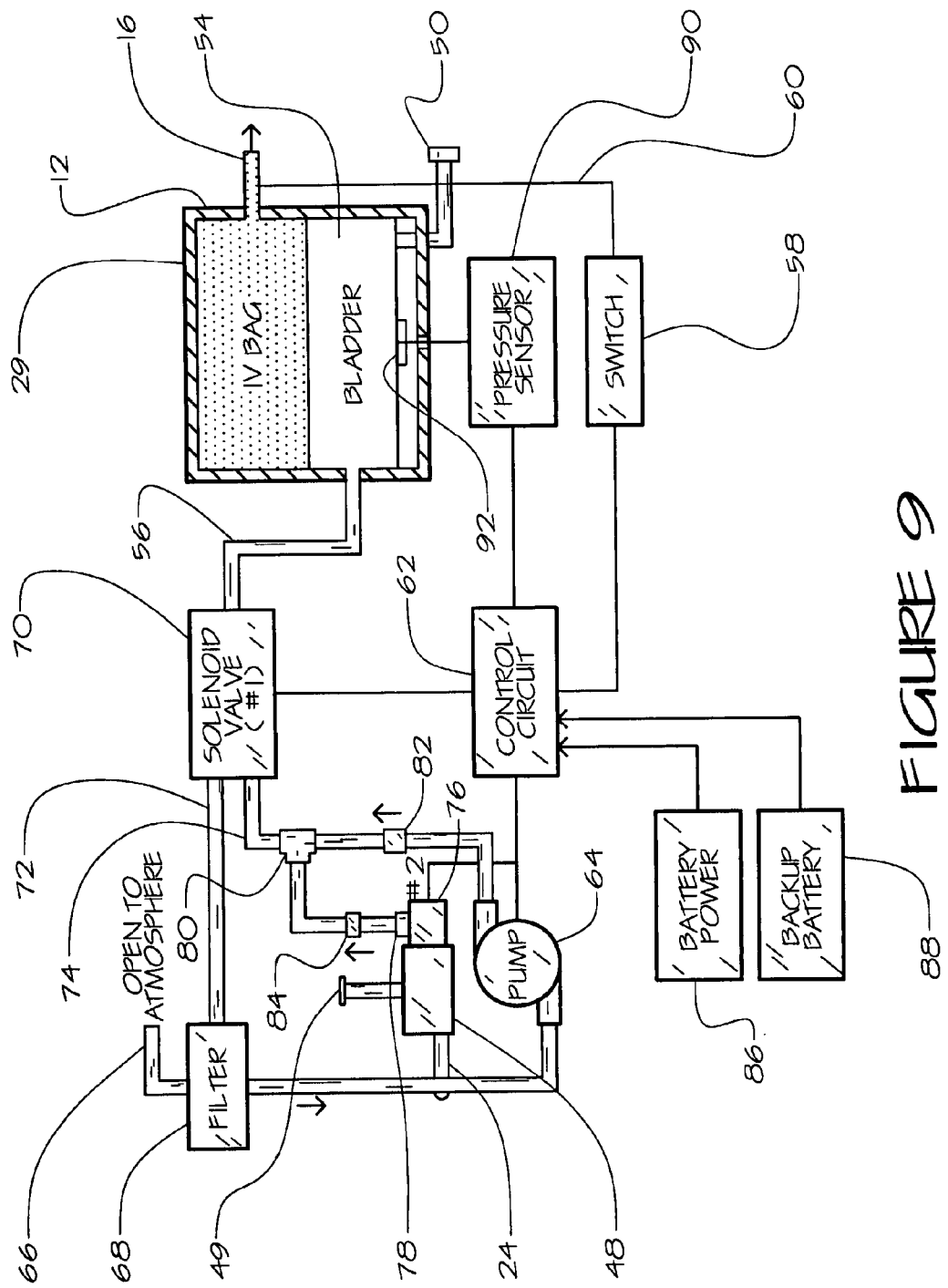
FIG. 9 is a schematic diagram of a control system for the infusion pump, indicating a pressure sensor and control and flow of gas to pressurize a bladder of the unit.

FIG. 9 shows flow of pressurizing gas, valves and control of the system. As described above, the IV solution bag 29 is placed against the inflatable bladder 54 in the housing 12, and the cover is closed. The bladder is inflated to a pressure that will put equal pressure in the IV bag 29, causing pressurized IV solution to be delivered out through the IV bag port 16, to be delivered through an IV tube to the patient. When the bag is positioned correctly and the IV tube spike has been correctly inserted to tap the bag and the cover is closed, a switch 58 is actuated, as indicated by the control line 60 leading from the port/dispensing spike area to the switch 58. This enables the system to operate to dispense solution, via the control circuit shown at 62. The control circuit turns on an electric air pump 64 when IV solution is to be delivered, and this may require a manual "on" switch to be engaged on the outside of the housing, such as located at 22 in FIG. 2, such switch being connected to the control circuit 62. The air pump 64 draws air from the atmosphere via an opening at 66, and the air may then filtered at 68. In this mode a three-way solenoid valve 70, valve No. 1, is positioned by the control circuit so as to close a venting line 72 and open an air supply line 74 to deliver gas under pressure via the line 56 to the bladder 54.

At the same time, the redundant gas cartridge system is also working. The compressed gas cartridge 24 puts out gas at high pressure (e.g. about 800 p.s.i), into the regulator 48. There, it is reduced greatly (to a pressure of, for example, about 30 psi). It then passes through another electrically operated valve 76, now opened under control of the control circuit 62. The gas, which is still at fairly high pressure, passes through a flow restrictor 78 just downstream of the valve 76, to slow the rate at which it can flow into the bladder. The gas then enters the fluid delivery line 74, through a T or Y connection 80 as shown. Note that check valves are included at 82 and 84, in both the electric air pump line and in the pressurized gas cartridge line, to prevent either source of pressure from pushing gas backward into the other.

In this way, both the air pump and the gas cartridge are delivering gas into the bladder simultaneously and as redundant systems, in a preferred embodiment. If the gas cartridge should be emptied, the air pump 64 will continue to operate. If the air pump 64 should malfunction, the gas cartridge will continue to supply the need of pressurized gas to the bladder. However, if the battery for the unit should go low, the gas cartridge alone could not operate the infusion pump. For this reason, in one embodiment the system may include main battery power indicated at 86 as well as a small back-up battery 88, with the control circuit 62 receiving and distributing power such that if main battery power 86 is out, the pump 64 will no longer be powered, but the control circuit and solenoid valves 70 and 76 will still be operable, as well as the pressure sensor device 90 which has a sensor in contact with the bladder at 92, and indicator lights.

When dispensing of IV solution is to cease, a switch in the housing is operated and the control circuit 62 shuts off the pump 64, closes valve No. 2 at 76, and simultaneously changes the position of valve No. 1 at 70, to close the gas inlet line 74 and to open the vent line 72 to the vent 66 so that pressure in the bladder is immediately vented to atmosphere, discontinuing pressure against the IV bag and thus ceasing delivery of IV solution. When the IV bag 29 empties, the control 62 senses this through a static reading at the pressure sensor, and shuts off the unit as just described.

The above described preferred embodiments are intended to illustrate the principles of the invention, but not to limit its scope. Other embodiments and variations to this preferred embodiment will be apparent to those skilled in the art and may be made without departing from the spirit and scope of the invention.

I claim:

1. An infusion pump for delivering intravenous solution from a solution bag through tubing to a patient, the bag having at least one flexible wall and having a dispensing port for releasable connection with an end of the tubing, comprising:

a housing with a compartment for removably receiving and supporting the intravenous solution bag in a solution-dispensing position, an expandable bladder mounted within the compartment and forming a part of the infusion pump, having a flexible wall which moves by expansion responsive to an increase in the pressure of a fluid within the bladder, the bladder being positioned in the housing so as to apply a pushing force against the flexible wall of a solution bag when present, to collapse the solution bag responsive to expansion of the bladder wall to cause solution within the bag to be infused out through the dispensing port, a sensor for sensing pressure in a solution bag when present, an electric pump connected to pump fluid into the bladder to increase pressure in the bladder in response to an electrical signal indicating the need for increased pressure, a gas cartridge containing high-pressure gas connected to the housing, with a pressure regulator connected to the gas cartridge to produce gas at greatly reduced pressure, said reduced-pressure gas being selectively connected to the bladder, and control means connected to the sensor and effective to send said electrical signal to send fluid to the bladder to increase pressure in the bladder when the sensor indicates pressure in the bladder is below a desired pressure preselected in the control means.

2. The apparatus of claim 1, wherein the electric pump is powered by batteries contained within the housing.

3. The apparatus of claim 1, including a flow restrictor connected downstream of the pressure regulator so as to slow the flow of reduced-pressure gas into the bladder.

4. The apparatus of claim 1, wherein the pressurized gas cartridge and the housing include a screw means for screwing the gas cartridge onto the housing from the exterior of the housing.

5. The apparatus of claim 4, wherein the screw means includes a gas cartridge-engaging capsule with screw threads, and cooperating screw threads in the housing to receive the gas cartridge as engaged by the threaded capsule.

6. The apparatus of claim 2, further including a back-up battery in the housing, connected to power the control means in the event the batteries powering the electric pump become inoperable, so that fluid pressure from the gas cartridge alone can provide pressure for the bladder.

7. The apparatus of claim 6, further including electrically operated valves connected to the control means, one electrically operated valve controlling flow from the gas cartridge and a second electrically operated valve having two positions, one for venting the bladder of pressure and the other for allowing gas from the pump for the gas cartridge to enter the bladder, and wherein the two electrically operated valves are connected to receive power from the back-up battery when needed.

8. The apparatus of claim 1, wherein the electric pump and the reduced pressure gas are both connected to deliver fluid to the bladder, and wherein the control means sends said signal to activate both the pump and the gas simultaneously.

9. The apparatus of the claim 1, wherein one of the electric pump and the gas cartridge comprises a primary pressure source, with the other pressure source not responding to said signal except when the primary pressure source is not operable, and including means for activating said other pressure source via said signal when the primary pressure source is not operable.

10. The apparatus of claim 1, further including an externally visible indicator on the housing to indicate remaining pressure in the gas cartridge.

11. The apparatus of claim 10, wherein the visible indicator comprises a spring-loaded plunger that extends outwardly to an extent indicating remaining pressure.

12. The apparatus of claim 1, further including a universal IV solution bag adapter in the housing, for receiving IV solution bags having ports in several different positions and for cradling the combination of an IV dispensing spike engaged with an IV bag port in a position of correct installation of the IV bag in the housing, and including a bag/spike-in-place switch actuator engageable by an IV dispensing spike which may be in different positions in the housing for different IV solution bags.

13. The apparatus of claim 12, wherein the switch actuator comprises an elongated depressable strip connected to a switch, the strip being positioned to be contacted by an enlarged collar of an IV dispensing spike which can be for different bags such that the spike and collar can be in either of at least two different positions.

14. The apparatus of claim 1, further including a manual venting valve extending exterior of the housing, the manual venting valve being connected by a tube to the bladder and enabling quick venting of the bladder by opening of the venting valve when the bladder needs to accommodate a full IV solution bag to be installed in the housing.

15. The apparatus of claim 1, further including a visible indicator at the exterior of the housing for indicating pressure remaining in the gas cartridge.

16. The apparatus of claim 15, wherein the visible indicator comprises a spring-loaded plunger that extends outwardly to an extent to quantitatively indicate remaining pressure.

17. An infusion pump for delivering intravenous solution from a solution bag through tubing to a patient, the bag having at least one flexible wall and having a dispensing port for releasable connection with an end of the tubing, comprising:

a housing with a compartment for removably receiving and supporting the intravenous solution bag in a solution-dispensing position, an expandable bladder within the compartment, having a flexible wall which moves by expansion responsive to an increase in the pressure of a fluid within the bladder, the bladder being positioned in the housing so as to apply a pushing force against the flexible wall of a solution bag when present, to collapse the solution bag responsive to expansion of the bladder wall to cause solution within the bag to be infused out through the dispensing port, a sensor for sensing pressure in a solution bag when present, fluid pressure means for delivering fluid under pressure into the bladder to increase pressure in the bladder in response to a signal indicating the need for increased pressure, control means connected to the sensor and effective to send said signal to send fluid to the bladder to increase pressure in the bladder when the sensor indicates pressure in the bladder is below a desired pressure preselected in the control means, and a universal IV solution bag adapter in the housing, the adapter having multiple, laterally displaced port notches positioned to receive differently-configured IV solution bags having solution dispensing ports in different lateral positions and for cradling the combination of an IV dispensing spike engaged with an IV bag solution dispensing port in a position of correct installation of the IV bag in the housing, and including a bag/spike-in-place switch actuator engageable by an IV dispensing spike which may, when engaged with different IV solution bags and placed in the adapter, be in different dispensing port positions relative to the housing.

18. The apparatus of claim 17, wherein the switch actuator comprises an elongated depressable strip connected to a switch, the strip being positioned to be contacted by an enlarged collar of an IV dispensing spike which can be for different bags such that the spike and collar can be in either of at least two different positions.

19. The apparatus of claim 17, further including a manual venting valve extending exterior of the housing, the manual venting valve being connected by a tube to the bladder and enabling quick venting of the bladder by opening of the venting valve when the bladder needs to accommodate a full IV solution bag to be installed in the housing.

20. The apparatus of claim 17, wherein the fluid pressure means comprises a compressed gas cartridge, and further including an externally visible indicator on the housing to indicate remaining pressure in the gas cartridge.

* * * * *